(12) United States Patent
Naeymi-Rad et al.

(10) Patent No.: US 11,488,690 B2
(45) Date of Patent: Nov. 1, 2022

(54) SYSTEM AND METHOD FOR PROBLEM LIST RECONCILIATION IN AN ELECTRONIC MEDICAL RECORD

(71) Applicant: Intelligent Medical Objects, Inc., Northbrook, IL (US)

(72) Inventors: Frank Naeymi-Rad, Libertyville, IL (US); Regis Chariot, Lake Bluff, IL (US); Jose A. Maldonado, Chicago, IL (US); James Thompson, St. Charles, IL (US); Fred Masarie, Husum, WA (US); Ivana Naeymi-Rad, Libertyville, IL (US); Alex Burck, Mount Prospect, IL (US)

(73) Assignee: Intelligent Medical Objects, Inc., Rosemont, IL (US)

( * ) Notice: Subject to any disclaimer, the term of this patent is extended or adjusted under 35 U.S.C. 154(b) by 787 days.

(21) Appl. No.: 14/530,727

(22) Filed: Nov. 1, 2014

(65) Prior Publication Data

US 2015/0242571 A1   Aug. 27, 2015

Related U.S. Application Data

(60) Provisional application No. 61/943,109, filed on Feb. 21, 2014.

(51) Int. Cl.
*G16H 10/60* (2018.01)
(52) U.S. Cl.
CPC .................................. *G16H 10/60* (2018.01)
(58) Field of Classification Search
None
See application file for complete search history.

(56) References Cited

U.S. PATENT DOCUMENTS

| 5,799,268 | A  | 8/1998 | Boguraev |
| 5,930,788 | A  | 7/1999 | Wical |
| 6,055,540 | A  | 4/2000 | Snow et al. |
| 6,101,515 | A  | 8/2000 | Wical et al. |
| 6,904,432 | B2 | 6/2005 | Chariot et al. |

(Continued)

OTHER PUBLICATIONS

"Semantic Web: Asking the Right Questions," Duch et al., Seventh International Conference on Information and Management Sciences, Urumchi, China, Aug. 12-19, 2008 entire document www.fizyka.umk.pl/ftp/pub/papers/kmk/08-SemWeb.pdf.

(Continued)

*Primary Examiner* — Devin C Hein
(74) *Attorney, Agent, or Firm* — Quarles & Brady LLP (57) ABSTRACT

A system and method for problem list categorization and management in an electronic health or medical record includes matching each entry in the list with an interface terminology concept, grouping related concepts together into one or more categories, and grouping entries into one or more nested sets of problems. Groupings are accomplished by analyzing semantic distances between concept elements to determine which entries are duplicates according to the interface terminology and which are different but related to sufficiently similar concepts. Certain elements will be sufficiently related that they are nested or clustered within a single problem list element. Others are different enough to merit different elements but classification within a common category of problems.

19 Claims, 7 Drawing Sheets

(56) References Cited

U.S. PATENT DOCUMENTS

| | | | |
|---|---|---|---|
| 7,167,858 B2 | 1/2007 | Naeymi-Rad et al. | |
| 7,496,593 B2 | 2/2009 | Gardner et al. | |
| 7,536,387 B2 | 5/2009 | Chariot et al. | |
| 7,693,917 B2 | 4/2010 | Chariot et al. | |
| 7,711,671 B2 | 5/2010 | Meyers | |
| 7,870,117 B1 | 1/2011 | Rennison | |
| 8,346,804 B2 | 1/2013 | Phillips | |
| 2002/0128861 A1 | 9/2002 | Lau et al. | |
| 2003/0179228 A1 | 9/2003 | Schreiber et al. | |
| 2005/0240572 A1 | 10/2005 | Sung et al. | |
| 2006/0069677 A1 | 3/2006 | Tanigawa et al. | |
| 2007/0179776 A1 | 8/2007 | Segond et al. | |
| 2008/0065452 A1 | 3/2008 | Naeymi-Rad et al. | |
| 2008/0306926 A1 | 12/2008 | Friedlander et al. | |
| 2009/0083231 A1 | 3/2009 | Eberholst et al. | |
| 2009/0150289 A1* | 6/2009 | Joe | G06F 19/322 705/50 |
| 2009/0254572 A1 | 10/2009 | Redlich et al. | |
| 2010/0169299 A1 | 7/2010 | Pollara | |
| 2010/0262659 A1 | 10/2010 | Christiansen et al. | |
| 2011/0066425 A1 | 3/2011 | Hudgins et al. | |
| 2011/0138050 A1 | 6/2011 | Dawson et al. | |
| 2011/0184960 A1 | 7/2011 | Delpha et al. | |
| 2012/0011124 A1* | 1/2012 | Bellegarda | G06F 17/3071 707/739 |
| 2012/0179696 A1* | 7/2012 | Charlot | G06F 17/30731 707/750 |
| 2012/0239671 A1* | 9/2012 | Chaudhri | G06Q 10/06 707/756 |
| 2013/0262142 A1* | 10/2013 | Sethumadhavan | G06F 19/3443 705/3 |
| 2013/0282713 A1* | 10/2013 | Lawrence | G06F 17/30867 707/732 |
| 2016/0019361 A1 | 1/2016 | Zasowski et al. | |

OTHER PUBLICATIONS

Virginia Tech SNOMED Core Structures 2nd AAHA Software Vendors Summit, Apr. 21, 2009.

"Social tagging overview (SharePoint Server 2010)" May 12, 2010 entire document http://technet.microsoft.com/en-us/library/ff608137.aspx.

Bronnert et al., Problem-Centered Care Delivery, Journal of AHIMA 83, No. 7 (Jul. 2012): 30-35.

\* cited by examiner

EHR Problem List

Top of Display

Personal history of methicillin resis staph infection

*Sensitive*

Bipolar disorder, unspecified

Cardiovascular

Congestive heart failure, unspecified CCM ...eans
Unspecified essential hypertension
Mitral valve insufficiency and aortic valve insufficiency
Atrial fibrillation

Endocrine

Type 2 diabetes mellitus without complication
Hyperlipidemia

Gastrointestinal

Esophageal Reflux
Ulcer of esophagus without bleeding
Constipation
Irritable bowel syndrome

Hematology/Oncology

Anemia

Musculoskeletal

Dorsalgia

Neuro

Epilepsy
Personal history of TIA

Renal

Urinary tract infection
Chronic kidney disease unspecified

Respiratory

Pneumonia, organism unspecified
ACE-inhibitor cough

Signs and Symptoms

Syncope and collapse

Other

Physical exam, annual

---

CCDA List for Import

Lower urinary tract infectious disease  4008004
Gastroesophageal reflux disease  235595009
Congestive heart failure  42343007
Constipation  14760008
Depressive disorder  35489007
Seizure disorder  128613002
Hypothyroidism  40930008
Atrial Fibrillation  49436004
Sinusitis  36971009
Essential hypertension  59621000
Acute upper respiratory infection  54398005
Methicillin resistant staph aureus carrier  432415000
Renal impairment  236423003

Reconciled Problem List

Top of Display

Personal History of Methicillin Resistant Staph...

*Sensitive*

Bipolar Disorder Unspecified

Cardiovascular

Congestive Heart Failure Unspecified COM ...more
Unspecified Essential Hypertension
Atrial Fibrillation
Mitral Valve Insuff&Aortic Valve Insuff

Endocrine

Type 2 diabetes mellitus without complication
Hyperlipidemia
Hypothyroidism

Gastrointestinal

Esophageal Reflux
Ulcer of Esophagus Without Bleeding
Constipation
Irritable Bowel Syndrome

HematologyOncology

Anemia

Musculoskeletal

Dorsalgia

Neuro

Epilepsy
Personal history of TIA

Renal

Lower urinary tract infectious disease
Renal Impairment

Respiratory

Pneumonia, Organism Unspecified
Cough, persistent
Sinusitis

Signs and Symptoms

Syncope and Collapse

Other

Annual Physical Exam

FIG. 7

SYSTEM AND METHOD FOR PROBLEM LIST RECONCILIATION IN AN ELECTRONIC MEDICAL RECORD

This application claims priority to U.S. provisional application 61/943,109, filed Feb. 21, 2014, which is incorporated herein by reference.

BACKGROUND OF THE INVENTION

Patient electronic medical records (EMRs) are used to store a patient's medical history in one location. EMRs permit more complete recordkeeping, which may lead to improved patient care, as healthcare professionals may be able to quickly and thoroughly review the patient's previous and current medical conditions in one location. EMRs also may facilitate portability of healthcare records.

As computer use has become more prevalent, electronic health records or electronic medical records (EHRs or EMRs) have become the industry standard for documenting patient care. Industry initiatives and government legislation have facilitated EHR implementation and use. Most notable among them is the Health Information Technology for Economic and Clinical Health Act (HIT ECH), which gives incentives to providers toward implementation and demonstration of meaningful EHR use.

An aspect of reliable and accurate information is ensuring that providers have the ability to capture their clinical intentions regarding patient care through terminologies. Healthcare terminology has long been called "the language of medicine," but, in the electronic age, this language has to be readable by both humans and computers. Various terminologies are used in defining associated terms.

Terminology

Terminology is a set of descriptions used to represent concepts specific to a particular discipline. It also is the foundation of EHR data. For example, the terms "heart attack" and "MI" describe the same concept of myocardial infarction. The concept in turn may be associated with codes that are used for a variety of purposes.

Different healthcare terminologies may have their own unique features and purposes. For example, one set of terminologies, RxNorm, encodes medications, while another set of terminologies, e.g., Logical Observation Identifiers Names and Codes (referred to under the trademark "LOINC"), is used for laboratory results.

Terms related to terminology include: Administrative code sets; Clinical code sets; and Reference terminologies.

Administrative code sets may be designed to support administrative functions of healthcare, such as reimbursement and other secondary data aggregation. Common examples are the International Classification of Disease (ICD) and the Current Procedural Terminology, which is referred to via the trademark CPT. Each system may be different, e.g., ICD's purpose is to aggregate, group, and classify conditions, whereas CPT is used for reporting medical services and procedures.

Clinical code sets have been developed to encode specific clinical entities involved in clinical work flow, such as LOINC and RxNorm. Clinical code sets have been developed to allow for meaningful electronic exchange and aggregation of clinical data for better patient care. For example, sending a laboratory test result using LOINC facilitates the receiving facility's ability to understand the result sent and make appropriate treatment choices based upon the laboratory result.

A reference terminology may be considered a "concept-based, controlled medical terminology." The Systematized Nomenclature of Medicine Clinical Terms (referred to under the trademark "SNOMED CT") is an example of this kind of terminology. It maintains a common reference point in the healthcare industry. Reference terminologies also identify relationships between their concepts. Relationships can be hierarchically defined, such as a parent/child relationship. The reference terminology contains concept A and concept B, with a defined relationship of B as a child of A. SNOMED CT includes concepts such as heart disease and heart valve disorder, and their defined relationship identifies heart valve disorder as a child of heart disease.

Reference terminology may allow healthcare systems to get value from clinical data coded at the point of care. In general, reference terms may be useful for decision support and aggregate reporting and may be more general than the highly detailed descriptions of actual patient conditions. For example, one patient may have severe calcific aortic stenosis and another might have mild aortic insufficiency; however, a healthcare enterprise might be interested in finding all patients with aortic valve disease. The reference terminology creates links between "medical concepts" that allow these types of data queries.

One method of managing these various terminologies may involve generating an interface terminology configured to capture each user's clinical intent. The reference terminology may include a plurality of domains (problem, plan, medication, etc.), a plurality of unique concepts within each domain, and one or more descriptions mapped to each concept, where each description represents an alternative way to express a concept, and where each description captures various users' clinical intent. Exemplary methods for managing multiple terminologies through the use of an interface terminology may be found in the commonly owned U.S. patent application Ser. No. 13/660,512, the contents of which are incorporated herein by reference.

While EHRs aggregate patient information into a single location, they may suffer from information overload. For example, an EHR may include a patient problem list. Every time the patient indicates that he or she has a problem, that problem may get added to the patient list, causing the list to grow. Other types of additions include automated additions or additions to the problem list from multiple caregivers given access to modify the same list. Over time, this list may contain many entries, including duplicate problems, inaccurate problems, and outdated or resolved problems.

Similarly, because the problem list includes all of the patient's stated problems, it may contain information that, while current and unique, may not be that useful to the practitioner, particularly when the practitioner is a specialist. At the same time, the problems that actually are most useful to the practitioner may be overlooked or otherwise missed when the practitioner is reviewing the entire problem list.

In addition, while one of the benefits of an EMR is record portability, difficulties may arise when problem lists from multiple sources are combined, particularly if those lists come from different types or formats of EMRs, or contain problems that are represented within multiple different reference vocabularies.

What are needed are a system and method that address one or more of the issues presented above in order to present a clearer picture of the patient's problems.

BRIEF SUMMARY OF THE INVENTION

In one aspect, a system and method for problem list categorization may include matching each entry in the list with an interface terminology concept, grouping related concepts together into one or more categories, where the groupings are accomplished by analyzing semantic distances between concept elements, and grouping entries into one or more nested sets of problems. Nested elements—problems similar enough so that only one of several problems relates to the same concept—can be accomplished by having the semantic distances between problems drive a process that lets a clinician elect to display a summary list that has closely-related problems grouped "behind" a parent problem. For example, a "parent" problem of Diabetes might have "Diabetic retinopathy" and "Diabetic neuropathy" nested behind "Diabetes." This allows for both a summary view and an expanded view when a clinician wants full detail.

Problem list elements already may be tagged or coded with one or more terminologies, including administrative, clinical, and reference terminologies. The method may include determining a mapping between these terminologies and interface terminology concepts in order to determine which interface terminology concepts apply.

In another aspect, the system and method may include reconciling a plurality of problem lists into a single, unified list. As in the first aspect, the problem list elements may be arranged into one or more different categories, and the elements from both lists may be mapped to interface terminology elements to accomplish this task. As a result of this mapping, it may be possible to determine duplicates between the two lists, as well as determine entries that are not duplicates but that may be related to one another (either as belonging as separate entries within the same category or belonging as nested entries within that category). The lists then may be reconciled by removing duplicates, adding new entries from the secondary list to the primary list, and grouping the non-duplicate entries together.

Features and advantages are described in the following description, with reference to the accompanying drawings.

DETAILED DESCRIPTION

Figure 1:
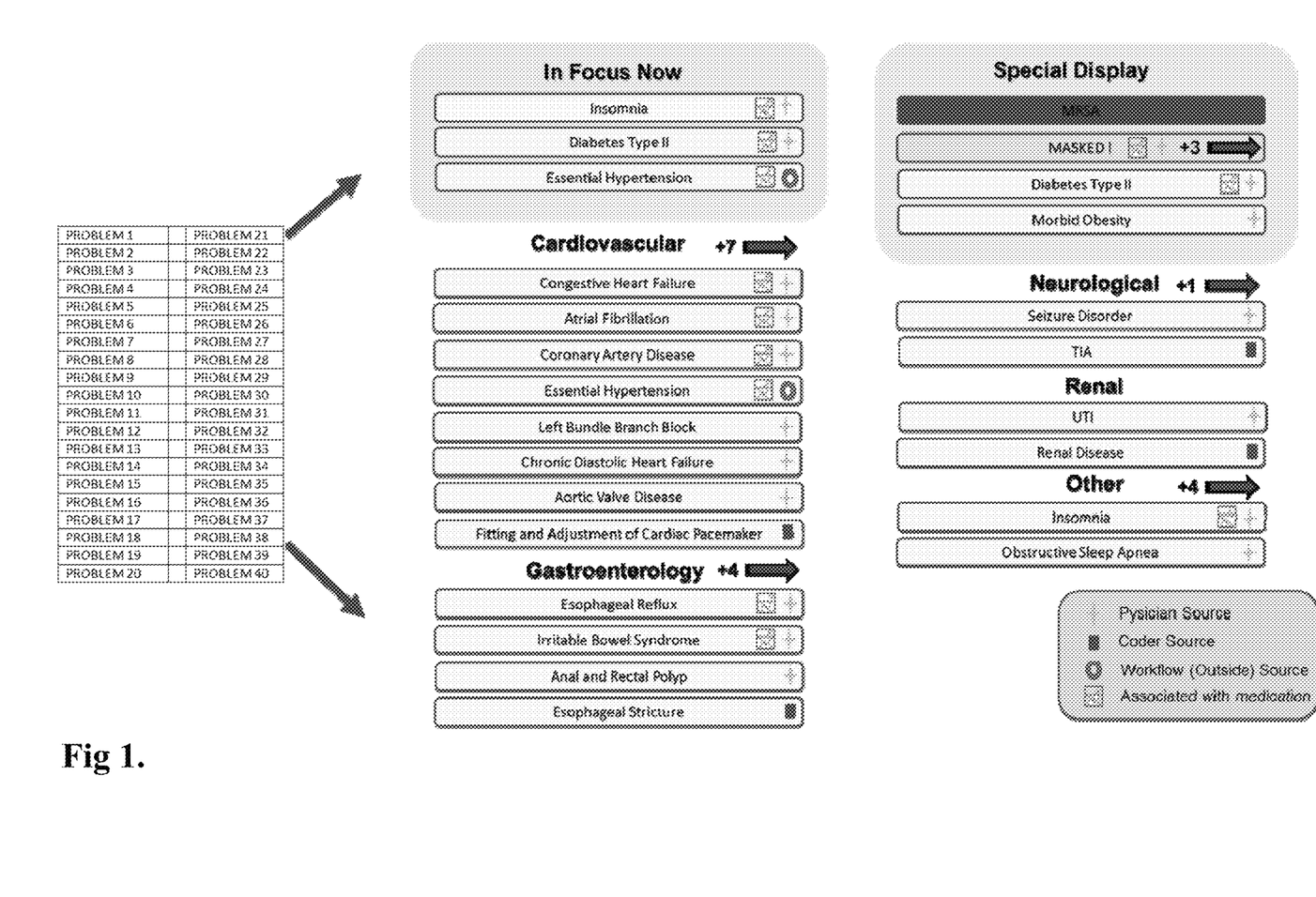
FIG. 1 is a depiction of a method of reconciling a general problem list into one or more clinical categories based on concept groupings. In this case the concept group is related to clinical specialties such as Gastroenterology or Cardiovascular. Many different concept groupings can be enabled using the methods described.

As seen in FIG. 1, a method for processing electronic medical record problem lists may be employed to generate a clinically relevant patient profile. In one aspect, the patient profile may be useful to a clinician because it may categorize and group related problems according to concept groupings, and groupings may be determined based on semantic distance between the represented concepts. For example, all cardiovascular problems may be grouped under a "cardiovascular" category, all kidney-related problems may be grouped under a "renal" category, etc.

Figure 2:
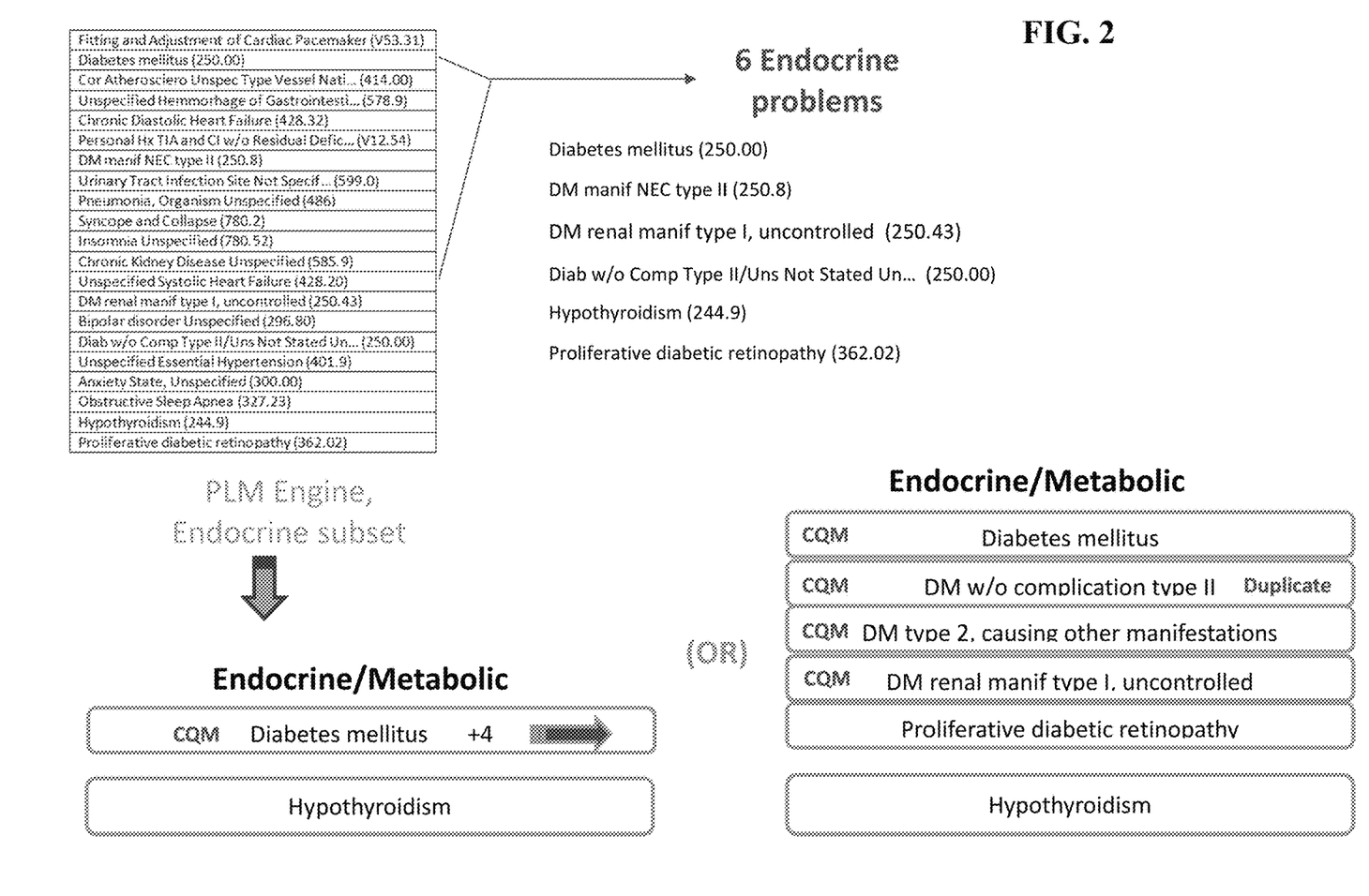
FIG. 2 is a depiction of exemplary relationships between problem list elements within a clinical category and an example of how problems can be nested together or seen in full detail.

In addition, the system may attach indicator flags to the problems within each category, which may permit later ranking and ranked display of the problems according to attributes, such as severity, timeliness, or other concepts such as classification within a clinical measure. One example of such a flag is seen in FIG. 2, in which the problem "Diabetes mellitus" and the related problems clustered underneath that summary problem are marked with a CQM flag. The system may apply an indicator flag to the summary problem if any of its clustered problems (as that term is discussed in greater detail below) include the flag.

The CQM, i.e., Clinical Quality Measurement, flag indicates that its associated problem element must comply with CQM requirements for treatment and documentation in order to be eligible for the reimbursements provided for such compliance. Thus, a problem having this flag may be presented to the user as a higher value or higher priority problem element. In addition to having the flag callout, this flag also may be used as a factor in problem list ranking. For example, CQM problems may be ranked and presented higher on the problem list within each category than other, non-flagged problem elements.

Other potential flags may include HCC (Hierarchical Condition Category), CC (Complication and Comorbidity), and MCC (Major Complication and Comorbidity). One of ordinary skill in the art would appreciate that values associated with these terms are reflective of the severity of their underlying problems. As such, problems flagged with one or more of these flags may provide a visual indicator to the user that they may need to be addressed with higher priority than other problems on the list.

Returning to FIG. 1, multiple criteria in addition to the indicator flags may be applied to the problems in order to determine the rankings within these lists. For example, problems that are associated with/require medication may be ranked higher than those that are/do not. Problems that are entered by a physician/clinician may be ranked higher than those that are sourced from other entities later in the record review process, e.g., by a coder or other administrative personnel. Problems that are obtained from workflow or some other outsider source, e.g., those problems that may be extracted from review of the patient's chart may rank somewhere in between clinician- and coder-generated problems (assuming all other factors are the same). Problem entries may be time-stamped, such that more recent problems may be ranked higher than older problems.

The clinicians viewing the problem list then can see the problems that pertain to their specialty quickly and easily, e.g., a cardiologist can look for the cardiovascular category and then focus on its entries. In one aspect, the clinician may be able to set up a filter to display preferred problems or categories of problems, while excluding non-selected problems or categories from being displayed. In another aspect, clinicians may pre-establish a profile that includes details about their preferred practice area(s). Upon logging-on to the system, the clinician's personal information may be retrieved. When the clinician selects a patient's record, the system then may cross-check the clinician's profile with each of the categories of problems. The system then may display one or more problems or categories of problems that match that clinician's profile. In either case, the filter may function to bring a specialty-based problem view to the front of the clinician's review.

Other filters may include the option to show an expanded list that shows every problem in a category vs. a summary or nested list that shows the highest level problem for a group of problems within a category, with the other problems being closed off or otherwise hidden from view.

The system also enables identification of potentially sensitive problems, so that the EHR can mark them for special treatment such as a secondary layer of privacy for viewing, or special attention by the clinician who has access to the Problem List. Examples of "sensitive" problems include, e.g., HIV and mental illness. Marking a problem as sensitive may allow it to be masked from some users, thereby restricting access only to those who are authorized.

The system also may generate lists in order to call attention to problems that may require more immediate attention or problems that may affect multiple disciplines. For example, another possible category may be an "in focus now" category, which may display those problems currently most relevant to the user, regardless of whether the problem also can fit into one of the other categories described above, and a "special display" category, which may list high priority problems of extreme, immediate importance, or of problems which are always part of the patient's overall baseline health state. These problems may be categorized more specifically, but they may have effects that cross disciplines, such that the clinician may desire to know about them when addressing the specific problems within his or her discipline.

In another aspect, it may be desirable to refine the problem list by eliminating redundancies or categorizing which problems are resolved vs. which ones are chronic or ongoing, etc. The same or similar ranking criteria as those described above with regard to problem entries within each category may be applied to the problem list as a whole in order to rank the entries, regardless of categorization. Alternatively, the category that may apply to a particular problem also may serve as a criterion in this ranking analysis, e.g., a cardiac or neurological problem may be ranked higher than an orthopedic one.

The system may display or output each tagged problem using description elements within the interface terminology, i.e., alternative ways to express the concept, because this may better express clinical intent, particularly the intent of the entity that created the problem/added the problem to the patient's list.

The system also may include a map between the various concepts within the interface terminology and with elements of other, external terminologies and vocabulary datasets, such as ICD9, ICD10, SNOMEDCT, MeSH, and Clinical Quality Measure elements, etc. These mappings may be precompiled such that the system may avoid needing to remap relationships between interface terminology elements and the external sets when dealing with additional problem lists, e.g., the lists of other patients.

This mapping may serve as the basis for the categorization, grouping, rolling up, nesting, etc., of the entries in a problem list. Certain interface terminology concepts may be related to other interface terminology concepts based on similar subject matter. For example, there may be a plurality of concepts that pertain to cardiac conditions. Thus, all problems that map to these concepts may be grouped together for categorization and display such as that shown in FIG. 1.

In addition to the ranking or sorting criteria describe above, these outside vocabulary mappings may be an additional factor used to rank the problem list entries. For example, mappings to some established terminologies or vocabularies may be used to perform the mapping/grouping described in the previous paragraph, and mappings to a second terminology or vocabulary or a proprietary mechanism may be used to sort more specifically within the determined categories.

Turning now to FIG. 2, it will be seen that certain problems not only fall within the same category as other problems but that they also may be considered subsets of another problem, i.e., they may be clusters within that problem. These relationships can be determined and managed by using the interface terminology, which also may recognize that certain concepts are more general than others and thus are hierarchically related to those other concepts. The system may group these more specific concepts underneath the more general, parent concept, thereby further arranging the problem list, whose entries may be mapped to these sub-concepts. As it relates to presentation of these problem list entries, the system may display in the problem list the problem that maps to the more general, parent concept and an indicator that other problem entries are nested or clustered and may be viewable under that parent problem, e.g., by clicking on the indicator.

In one aspect, clustered problem elements underneath a more general, parent concept may be ranked or organized using one or more of the criteria discussed above for ranking elements within the problem list generally. Alternatively, as seen in FIG. 2, clustered problem elements may be arranged using a more simplistic algorithm, e.g., they may be arranged alphabetically. In still another aspect, the system may rank flagged problems above non-ranked problems and then apply the more simplistic algorithm within each of those subsets. In any event, the system may allow user customization, permitting the user to rearrange the ordering of elements both in the problem list and within the clustered subsets, as discussed below.

From a database management perspective, clustered problems may be stored as a list of elements in a flat file database, with each element pointing to its parent problem element. Alternatively, clusters may be sub-trees in a hierarchical database structure underneath their respective category elements.

To this point, the patient list has been described as being patient specific, i.e., each patient has his or her own list, with entries specific to that patient in order to accurately record the patient's problem history. The system and method may function similarly as a way to bring a clearer clinical picture for a population aggregator, i.e., determining what problems exist for a given population, or for a given patient who may have multiple problems culled from multiple sources within a large data warehouse. In that case, the number of problems in the aggregated list may be larger (likely significantly larger) than for an individual record within an EHR, although the methodology may remain the same, i.e., each problem may be mapped to an interface terminology concept, concepts may be grouped and ordered, and the ordered problems then may be available for logical display and analysis.

Figure 3:
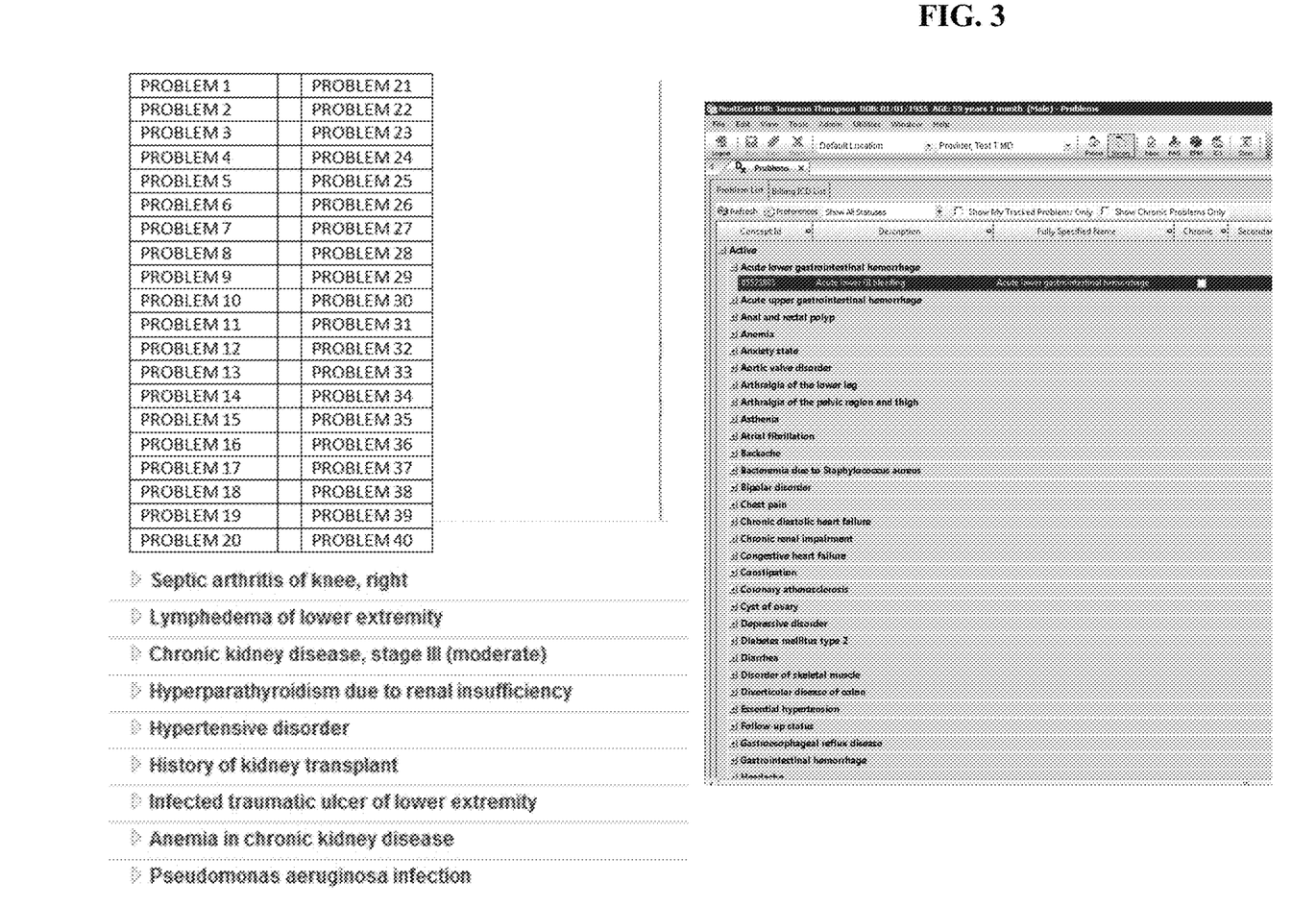
FIG. 3 is a depiction of problem lists from different sources, illustrating differences in the way in which problem list elements are arranged and displayed.

As seen in FIG. 3, and as discussed above, another issue with problem lists may become evident when attempts are made to combine lists from multiple different sources. These sources may format, store, and/or represent elements in the list differently from one another and not in a consistent format.

In order to accomplish reconciliation of elements within a single list (i.e., grouping problems within a list into categories and establishing clusters within those categories, which may or may not include the step of combining elements from multiple problem lists into a single list), the system may create an anchoring term from an interface terminology foundation technology that permits creation of a semantic distance between any two other terms from external vocabularies. This anchoring term may be considered a central concept within an interface terminology. In one aspect, determining this anchoring term may be achieved by a concept tagging method, and examples of such a method may be found in the commonly-owned co-pending U.S. application Ser. No. 13/004,128, the contents of which also are incorporated by reference.

For example, the process may comprise populating a database with a plurality of distinct concepts, populating a database with a plurality of descriptions, relating each description to a respective concept, reviewing the content (e.g., the problem list elements) for a satisfactory description match; and creating a tag for the satisfactory description match. Concepts may be well-defined clinical findings, i.e., items that are distinct by nature. Descriptions may comprise a plurality of words. Factors for determining whether the match is satisfactory may include whether there is a textual match between a portion of the content and the description and a distance between words in the content, the words corresponding to discrete words of each description.

Each concept may be part of a tree or hierarchy of other concepts, i.e., each concept preferably may have, at most, one parent concept, although it also may have multiple child concepts. A "Knee Pain" concept (term) may be expanded semantically to parent/child clinical concepts, including semantic distance that will help build the problem list ranking. For example, knee pain may be connected up to the broader concept of joint pain, which may be connected to musculoskeletal pain. Similarly, knee pain may be connected down to the more specific concepts of anterior knee pain and knee joint, painful on movement. This semantic difference may be expressed in terms of discrete positive or negative values away from the concept.

The heuristic that determines a problem's final ranking may be a function of description frequency and description presence factor, as well as the semantic difference or distance from other descriptions. Because multiple descriptions may relate to a shared concept, description frequency may be a compound value of all occurrences of all description variances of a shared concept, here, e.g., the concept of "Knee Pain." Relatedly, a term presence factor may reflect how "close" or "loose" a potential concept match may be. For example, the phrase "knee pain" may have a high term presence factor for the concept "knee pain," whereas the phrase "pain under kneecap" may have a lower term presence factor, reflecting the difference in terminology and inference that is required to make the match.

Thus, each problem list element is analyzed and tagged with a description that represents the clinical intent behind that element, the description being part of an interface terminology and mapping within that terminology to a concept, thereby normalizing the problem list elements. The problems then may be analyzed, using those concept tags, to determine if any relationship exists among them, e.g., whether they represent duplications or related concepts (broader than/less than/subset of), or whether they are unrelated. Once analyzed, the elements may be grouped and ranked as described above, for presentation to and review by the user.

Figure 4:
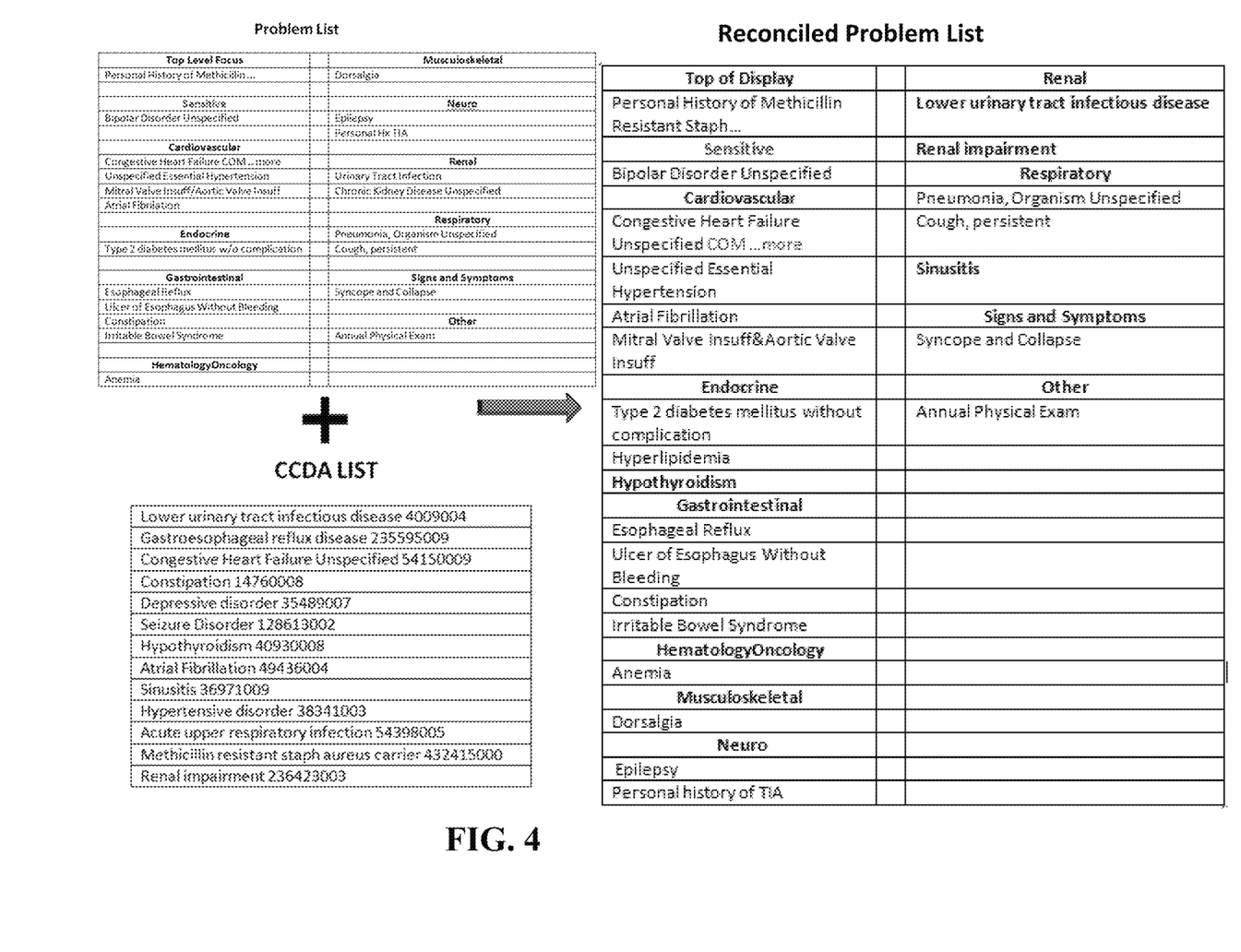
FIG. 4 is a depiction of the reconciliation of elements of multiple problem lists into a single, unified list.

Turning now to FIG. 4, the method may include incorporating and reconciling problem lists from multiple sources, e.g., from multiple EHR sources or from an EHR and from a Consolidated Clinical Document Architecture (CCDA) source. This latter case may be particularly useful in order to comply with Meaningful Use, Stage 2 (MU2) requirements, which require the ability to incorporate and reconcile an inbound CCDA problem list with the home EHR list. In still another example, the secondary list needing reconciliation may be generated by Natural Language Processing (NLP) suggestions.

As with a single problem list, the final product may be an ordered, categorized, clinical problem list. In addition to this ordering, however, the system may determine and reconcile conflicts or redundancies between multiple lists. Reconciliation may require the steps of: identifying which problems are identical; identifying which problems are closely related; and creating a mechanism to incorporate, preferably rapidly and accurately, reject, or refine both sets of problems into a new clinical set.

In this aspect, tools similar to those described above may be used to reconcile the multiple problem lists. For example, problems in each list may be tagged using a common interface terminology. Once this commonality has been established, the entries from the two lists may be combined into a single list using the interface terminology mappings as a guidebook.

One advantage of this type of reconciliation is that one of the two lists already may include mappings between the problems and some kind of code set. For example, the CCDA-structured problem list that complies with MU2 may have its problems coded with SNOMED-CT codes. As such, the analysis of the problems in that list may be simplified, because it may be easier to map the SNOMED-CT codes to interface terminology concepts than to do a mapping between the text of the problem and the interface terminology.

In addition, while this automated procedure may be able to reconcile problem lists with a high degree of accuracy and completeness (e.g., between about 90% and about 95%), the system may benefit from a human interaction component. As such, the system may include a package of refinement tools that may permit a user, e.g., a clinician that has the experience and knowledge, to evaluate potentially similar entries and determine what, if any, relationship might exist between those entries. For example, the user may be able to move an entry from one category into another, from no category to an existing category, or from an existing category into either a new category or into an undefined area. The user also may able to move the entry around within the category, e.g., moving it up or down to reflect a higher or lower priority, respectively, or determining that it belongs as a subentry of an already-existing problem.

Figure 5:
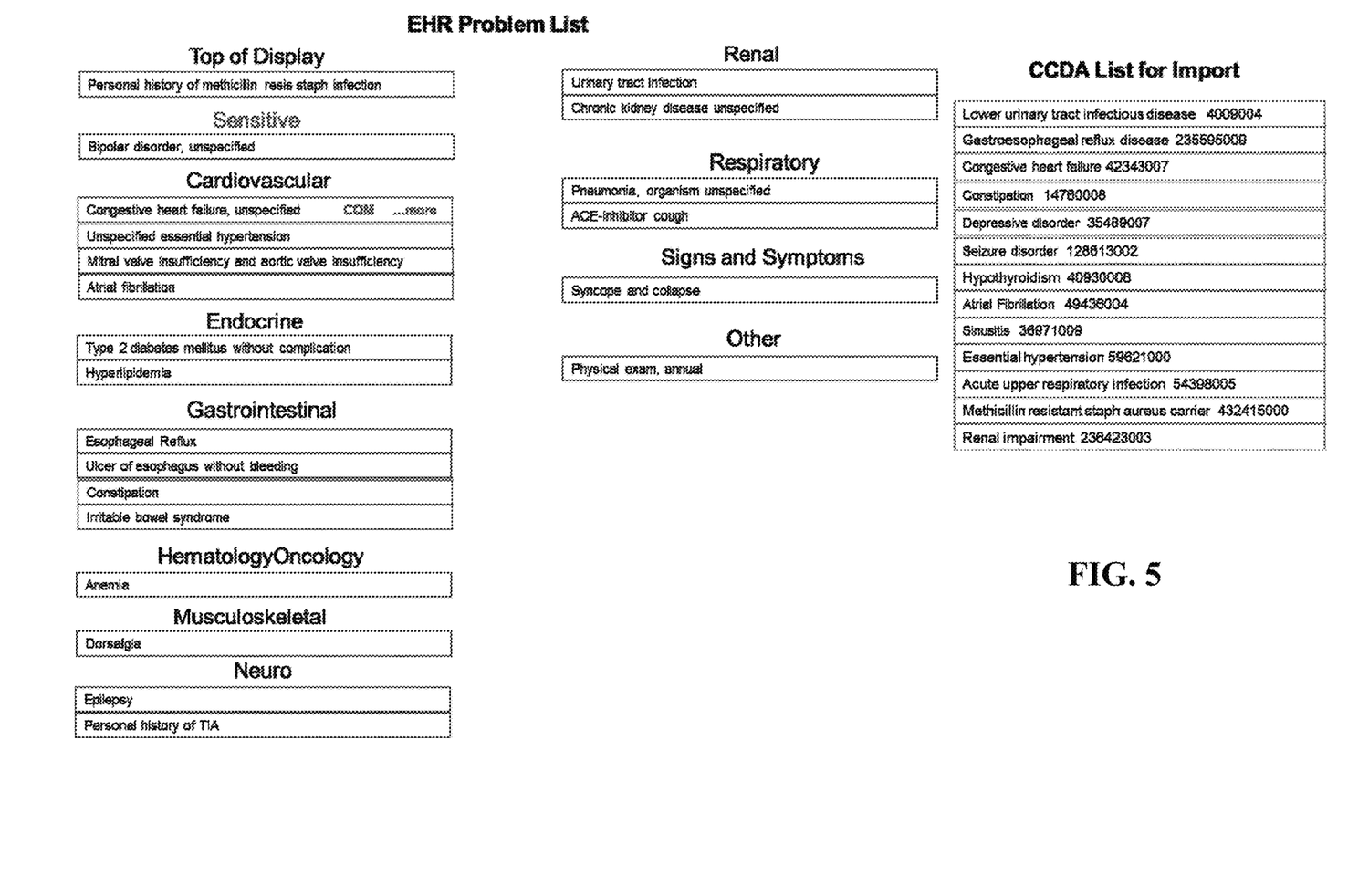
FIG. 5 illustrates two separate problem lists side-by-side, the lists requiring reconciliation, but the entries in the lists being seemingly rather different from one another.
Figure 6:
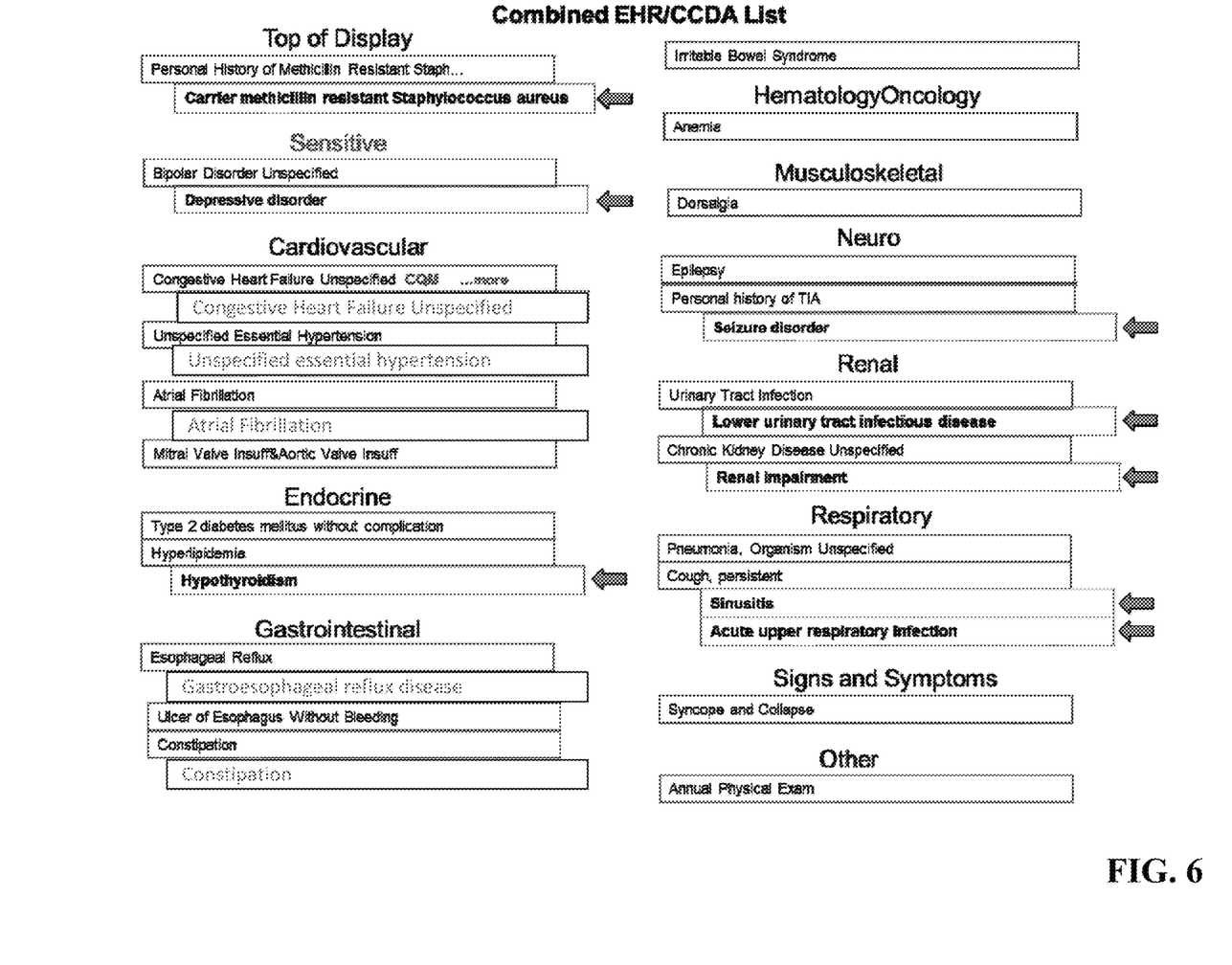
FIG. 6 illustrates the two lists mapped on top of one another, with duplicates highlighted in a first fashion and non-duplicates highlighted in a second fashion.

FIG. 5 shows one example of two lists for reconciliation side-by-side, e.g., an EHR list and a CCDA list for import. FIG. 6 then shows a presentation layer implementing one example of the reconciliation strategy. This presentation layer depicts the entries from the EHR as the left justified items and the CCDA entries as the right justified items. In addition, the system analyzes the data sets to determine whether, once the problems have been mapped to the interface terminology concepts, there are any duplicates. If so, the presentation layer may alert the user to the existence of the duplicates, e.g., by locating the duplicate next to the problem it matches and by graying it out or otherwise indicating that it should remain in that location and not be moved elsewhere.

In addition, the system may flag non-duplicates, e.g., with the indicator arrows shown in FIG. 6. As can be seen, the system already automatically may have determined that the non-duplicates belong in certain categories. In this case, the presentation layer may be used by the user to move the non-duplicates, either within the categories in which they were placed or to a different category altogether.

Figure 7:
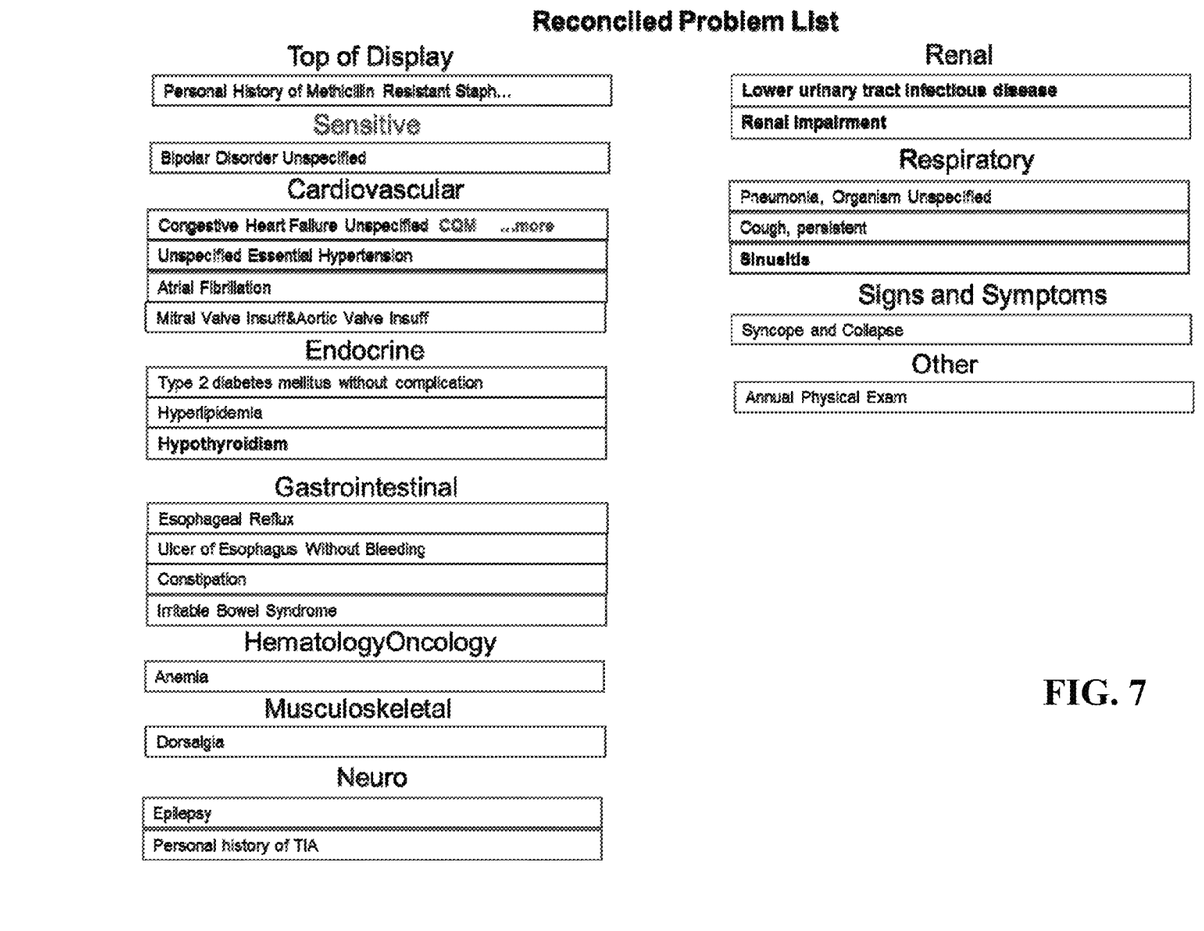
FIG. 7 is a depiction of a reconciled problem list created from the two lists in FIG. 5 using the methods described.

Turning now to FIG. 7, a reconciled problem list is shown, with the multiple lists combined into a single, comprehensive problem list. New entries may be shown in boldface or otherwise may be highlighted to alert the user to the additions. In addition, different term sets may be used on the problem list and may be presented to the user. In one aspect, the system may display the problems using the interface terminology concept labels that were applied to the problem entries. However, the system may also give the user an option to display the terms as they appeared in the lists prior to reconciliation, as those terms may more accurately reflect the clinical intent of the individual that generated the problem. In that case, the interface terminology mapping may remain in the background, such that the interface terminology terms may not be exposed to the end users.

The system may function as a separate widget or application accessible by an EHR software package. Preferably, however, this problem list analysis and reconciliation tool may be integrated into the EHR package.

In still another aspect, the system may recognize that certain combinations of problems may trigger one or more care plans. Thus, the system may analyze the various problem list entries to determine whether care plans are recommended and if so, which ones. This analysis may be performed using the interface terminology concepts tagged to each problem list element, which may increase processing efficiency since a comparison between those existing concepts and the various care plans may be precompiled and only may require, e.g., a simple table lookup, instead of requiring analysis and evaluation of non-normalized problem list terms as entered.

In conjunction with the organized problem list, the system then may output and display a care plan callout with indicators referring to the associated problems. For example, each care plan that the system recognizes may be displayed/highlighted/etc. in a distinct color, and the problems associated with a care plan similarly may be highlighted in the same color.

Additionally, depending on the number of problems in the list, the system may determine that multiple care plans are implicated. Thus, the system may rank those care plans, e.g., according to severity, timeliness, or other factors. Factors used in the ranking may include one or more of those discussed above for determining problem list rankings. In addition, the system may analyze the problems that trigger each care plan, using the rankings of those problems as a factor in ranking the care plans.

While the foregoing written description enables one of ordinary skill to make and use the same, those of ordinary skill also will understand and appreciate the existence of variations, combinations, and equivalents of the specific exemplary embodiments and methods disclosed herein. The claims should therefore not be limited by the above described embodiment and method but should be interpreted within the scope and spirit of the invention as claimed.

What is claimed is:

1. A method for displaying problem list entries in an electronic medical record or an electronic health record on a graphical user interface, comprising:
   mapping, using a computer, entries in the problem list with a respective description in an interface terminology, wherein the interface terminology comprises a plurality of domains, a plurality of concepts, and a plurality of descriptions, wherein each concept is unique within a given domain, and wherein each description maps to a respective concept in the interface terminology and is an alternative way to express the respective concept;
   analyzing, by a computer, interface terminology concepts mapped to each mapped entry to determine duplicate entries, where duplicate entries may be textually different but may map to the same interface terminology concept;
   analyzing, by a computer, interface terminology concepts mapped to each mapped entry to determine related entries;
   grouping related entries into one or more categories;
   ranking entries within the one or more categories;
   accessing a user profile stored on a computer; and
   displaying each category of related entries in separate regions of the graphical user interface, each region including a unique header and the respective ranked entries in ranked order, wherein the categories are dynamically arranged in the user interface in accordance with the user profile.

2. The method of claim 1, further comprising:
   ranking the categories with respect to one another.

3. The method of claim 1, wherein the ranking step includes attaching a flag to the entry, the flag indicating a severity of, or a documentation requirement related to, a problem list entry.

4. The method of claim 1, wherein a factor used in executing the ranking step is a date of creation for each entry.

5. The method of claim 1, wherein a factor used in executing the ranking step is an identity of the creator of each entry.

6. The method of claim 1, wherein the grouping step includes analyzing semantic distances between concepts mapped to the problem list entries.

7. The method of claim 6, wherein, based on the semantic distances, certain problem list entries are clustered as a subset within a parent entry.

8. The method of claim 7, wherein clustered entries are stored as a list of elements in a flat file database, with each element pointing to the parent entry.

9. The method of claim 7, wherein clustered entries are stored as a tree in a hierarchical database structure underneath a respective parent entry element.

10. The method of claim 1, wherein the entries originate in multiple problem lists, the method comprising:
    consolidating, using a computer, the multiple problem lists into a single list.

11. The method of claim 1, further comprising:
    filtering, by a computer, the entries in the problem list according to criteria pertaining to a viewer; and
    displaying only the filtered entries to the viewer.

12. The method of claim 1, further comprising:
assigning user rights to each potential viewer of the problem list;
flagging one or more problems as sensitive or having restricted access; and
restricting user access for each potential viewer to only those problems for which the user rights meet or exceed the respective flags.

13. A method for displaying problem list entries in an electronic medical record or an electronic health record on a graphical user interface, comprising:
normalizing, using a computer, entries in the problem list;
analyzing, by a computer, each normalized entry to determine duplicate entries, where duplicate entries may be textually different but may map indirectly to the same interface terminology concept, and where the interface terminology concept is part of an ontology that comprises a plurality of domains, a plurality of concepts, and a plurality of descriptions, wherein each concept is unique within a domain, and wherein each description is an alternative way to express a respective concept;
analyzing, by a computer, each mapped entry to determine related entries; and
grouping related entries into one or more categories;
accessing a user profile stored on a computer; and
displaying each category of related entries in separate regions of the graphical user interface, each region including a unique header and the respective ranked entries in ranked order,
wherein the categories are dynamically arranged in the user interface in accordance with the user profile, and
wherein the grouping step includes establishing an anchoring term concept from the interface terminology and analyzing semantic distances between concepts mapped to the problem list entries and the anchoring term.

14. The method of claim 13, wherein the normalizing step includes mapping each problem list entry to a respective description in an interface terminology.

15. The method of claim 13, further comprising:
ranking entries within the one or more categories.

16. The method of claim 15, further comprising:
ranking the categories with respect to one another.

17. The method of claim 13, wherein, based on the semantic distances, certain problem list entries are clustered as a subset within a parent entry.

18. The method of claim 17, further comprising:
flagging, by a computer, at least one clustered list entry with a flag indicating a severity of, or a documentation requirement related to, the entry; and
marking the parent entry with the same flag.

19. A method for displaying problem list entries in an electronic medical record or an electronic health record on a graphical user interface, comprising:
mapping, using a computer, entries in the problem list with a respective description in an interface terminology, wherein the interface terminology comprises a plurality of domains, a plurality of concepts, and a plurality of descriptions, wherein each concept is unique within a given domain, and wherein each description maps to a respective concept in the interface terminology and is an alternative way to express the respective concept;
analyzing, by a computer, interface terminology concepts mapped to each mapped entry to determine duplicate entries, where duplicate entries may be textually different but may map to the same interface terminology concept;
analyzing, by a computer, interface terminology concepts mapped to each mapped entry to determine related entries;
grouping related entries into one or more categories;
ranking entries within the one or more categories;
accessing a user profile stored on a computer; and
displaying each category of related entries in separate regions of the graphical user interface, each region including a unique header and the respective ranked entries in ranked order, wherein the displaying step comprises cross-checking the categories with the user profile and dynamically displaying the categories on the graphical user interface in accordance with the user profile.

* * * * *

UNITED STATES PATENT AND TRADEMARK OFFICE
CERTIFICATE OF CORRECTION

| | | |
|---|---|---|
| PATENT NO. | : 11,488,690 B2 | Page 1 of 1 |
| APPLICATION NO. | : 14/530727 | |
| DATED | : November 1, 2022 | |
| INVENTOR(S) | : Frank Naeymi-Rad et al. | |

It is certified that error appears in the above-identified patent and that said Letters Patent is hereby corrected as shown below:

On the Title Page

Item (72) In The Inventors:
"Regis Chariot" should be --Regis Charlot--

Signed and Sealed this
Thirtieth Day of May, 2023

Katherine Kelly Vidal
Director of the United States Patent and Trademark Office